US009339353B2

(12) United States Patent
Voudouris

(10) Patent No.: US 9,339,353 B2
(45) Date of Patent: May 17, 2016

(54) ACTIVE SELF-LIGATING BRACKET

(71) Applicant: Orthoarm Inc., Toronto (CA)

(72) Inventor: John Voudouris, Toronto (CA)

(73) Assignee: Orthoarm, Inc., Toronto (CA)

( * ) Notice: Subject to any disclaimer, the term of this patent is extended or adjusted under 35 U.S.C. 154(b) by 47 days.

(21) Appl. No.: 13/852,351

(22) Filed: Mar. 28, 2013

(65) Prior Publication Data

US 2013/0260329 A1    Oct. 3, 2013

Related U.S. Application Data

(60) Provisional application No. 61/616,462, filed on Mar. 28, 2012.

(51) Int. Cl.
*A61C 3/00* (2006.01)
*A61C 7/28* (2006.01)
*A61C 7/30* (2006.01)
A61C 7/20 (2006.01)

(52) U.S. Cl.
CPC . *A61C 7/287* (2013.01); *A61C 7/30* (2013.01); A61C 7/20 (2013.01)

(58) Field of Classification Search
CPC ............. A61C 7/20; A61C 7/287; A61C 7/30
USPC ....................................... 433/9–15
See application file for complete search history.

(56) References Cited

U.S. PATENT DOCUMENTS

| 4,197,642 | A | * | 4/1980 | Wallshein ....................... 433/11 |
| 4,712,999 | A |   | 12/1987 | Rosenberg |
| 5,474,445 | A |   | 12/1995 | Voudouris |
| 5,474,446 | A | * | 12/1995 | Wildman et al. ................ 433/14 |
| 5,613,850 | A | * | 3/1997 | Wildman et al. ................ 433/10 |
| 5,630,715 | A |   | 5/1997 | Voudouris |
| 5,857,850 | A |   | 1/1999 | Voudouris |
| 5,908,293 | A |   | 6/1999 | Voudouris |
| 5,913,680 | A |   | 6/1999 | Voudouris |
| 6,168,428 | B1 |   | 1/2001 | Voudouris |
| 6,257,883 | B1 |   | 7/2001 | Voudouris |
| 6,302,688 | B1 |   | 10/2001 | Jordan et al. |

(Continued)

*Primary Examiner* — Cris L Rodriguez
*Assistant Examiner* — Mirayda A Aponte
(74) *Attorney, Agent, or Firm* — McMillan LLP

(57) ABSTRACT

An orthodontic bracket including a body including a bonding base for attachment to the tooth, a lingual vertical slot, a pair of laterally spaced gingival tie wings and a pair of laterally spaced occlusal tie wings, the gingival and occlusal tie wings projecting from a labial surface of the body; an archwire slot extending mesio-distally across the body and between the gingival and occlusal tie wings at opposed medial and distal sides of the body to accommodate an archwire; a locking shutter including at pair of resilient arm members and a lingual guide bar between the resilient arm members, the locking shutter moveable between an open position in which placement and removal of the archwire is facilitated and a closed position in which placement and removal of the archwire is inhibited; first and second tracks formed on each of first and second outer lateral surfaces of the body, extending from the gingival tie wings across the archwire slot and into the occlusal tie wings; the first and second tracks sized and otherwise dimensioned to receive the pair of resilient arm members therein. The first and second tracks extend in a substantially occlusal-gingival direction, angled gingivally by an angle θ with respect to a plane parallel with the vertical plane of a tooth on the outer lateral surfaces such that the first and second tracks.

9 Claims, 10 Drawing Sheets

(56) References Cited

U.S. PATENT DOCUMENTS

| | | |
|---|---|---|
| 6,368,105 B1 | 4/2002 | Voudouris |
| 6,554,612 B2 | 4/2003 | Georgakis et al. |
| 6,582,226 B2 | 6/2003 | Jordan et al. |
| 6,843,651 B2 | 1/2005 | Orikasa |
| 6,939,133 B2 | 9/2005 | Voudouris |
| 6,984,127 B2 | 1/2006 | Lai |
| 7,014,460 B2 | 3/2006 | Lai et al. |
| 7,063,531 B2 | 6/2006 | Maijer |
| 7,186,114 B2 | 3/2007 | Navarro |
| 7,192,274 B2 | 3/2007 | Stadtmiller et al. |
| 7,214,057 B2 | 5/2007 | Voudouris |
| 7,267,545 B2 * | 9/2007 | Oda ................................ 433/10 |
| 7,442,039 B2 | 10/2008 | Opin et al. |
| 7,585,171 B2 | 9/2009 | Hagelganz et al. |
| 7,674,110 B2 | 3/2010 | Oda |
| 7,780,443 B2 | 8/2010 | Hagelganz et al. |
| 7,878,802 B2 | 2/2011 | Hagelganz et al. |
| 7,909,603 B2 | 3/2011 | Oda |
| 2006/0110699 A1 | 5/2006 | Forster |
| 2006/0228662 A1 * | 10/2006 | Lokar et al. ........................ 433/8 |
| 2006/0228664 A1 * | 10/2006 | Castner et al. .................... 433/11 |
| 2006/0269895 A1 | 11/2006 | Voudouris |
| 2009/0170049 A1 | 7/2009 | Heiser |
| 2010/0311004 A1 | 12/2010 | Voudouris |
| 2011/0076633 A1 * | 3/2011 | Bryant et al. .................... 433/11 |
| 2013/0236847 A1 | 9/2013 | Shin |

* cited by examiner

ACTIVE SELF-LIGATING BRACKET

RELATED APPLICATIONS

This application claims priority to U.S. Provisional Application No. 61/616,462 filed Mar. 28, 2012; the contents of which are herein expressly incorporated by reference.

FIELD OF THE INVENTION

The present invention relates to the field of orthodontic brackets, and more particularly to a self-ligating bracket having active archwire retention.

BACKGROUND OF THE INVENTION

Orthodontic treatment is effected by fixing small appliances often referred to as orthodontic brackets to a patient's teeth in an appropriate manner so as to correct malaligned teeth by applying an external force thereto through an archwire extending between the generally fixed orthodontic brackets. Directions mesial and distal mean generally left to right. Labial is the front surface, while lingual is defined as anything toward the direction of the tongue and it thereby stands to reason the word lingual is definitively and additionally defined as behind the labial surface. As to the structure of these orthodontic brackets, they are constructed of a body having small slots and are adhered directly on the labial or lingual sides of the teeth or welded to metal bands attached to the teeth by cementing or by some other method, as is generally known in the art.

As the form of use of the orthodontic bracket constructed as described above, a flexible archwire, which is curved so as to conform to a dental arch, is placed in an archwire slot in the bracket, and the tooth can be shifted over time by the restoring force of the archwire so that the teeth become well aligned. With the orthodontic bracket, a force can be applied to the tooth in a desired direction to correct the direction in which the tooth is shifted, rotated, tipped or torqued. This is effected by the three-dimensional inclination of the slot formed in the bracket body or by the desired bending of the archwire. Light, continuous forces are desirable for ideal biological movement that also reduce the risk of root resorption (root shortening).

Orthodontic treatment is accomplished by transmitting the restoring force of the archwires through brackets to the tooth roots. Generally, in an early period of the treatment, a thin, highly flexible round archwire is used, and an operation is required to loosen the ligature wire after ligating it such that the round wire freely slides within the slot (on a very low frictional basis). As treatment progresses, a thicker wire, a square or rectangular wire, and a more highly rigid wire eventually is used. When the alignment is nearly completed, the teeth are held for a while to prevent relapse. At this time, there are cases where the tooth is strongly fastened by a ligature wire so that it practically does not shift.

Various types and designs of self-ligating brackets are known in the art that provide different advantages, or solve particular problems depending on the patient's oral physiology. One type of self-ligating bracket uses a slider mechanism, such as a flat cap or plate that slides lineally within grooves or guides, to retain the archwire in the archwire slot. At one end of the slider mechanism's range, the archwire slot is closed and at the other, it is open. Any of a variety of structures can be used to bias or retain the slider mechanism in its open or its closed position. The invention provides an improvement to this type of passive self-ligating bracket.

One example of this type of bracket is shown in U.S. Pat. No. 6,168,428 to John Voudouris issued Jan. 2, 2001, and specifically at FIGS. 48 to 52. In this bracket, a spring member in the form of a resilient shim 720 located lingually to the labial face of the bracket, projects gingivally and has a jog directed lingually toward the archwire slot 3240d and presents a generally convex surface 722 towards the archwire slot 3240d. The gingival edge 724 of the shim 720 recurves labially.

As the arms 3540 slide within the slots 3530 to move the clip 3538 to a closed position as shown in FIG. 49, the convex surface 722 of the shim 720 engages the archwire 3242d and provides a continuous biasing action against the archwire. As may be seen in FIG. 51, the resilience of the shim 720 allows the orthodontic bracket 3220d to accommodate different sizes and configurations of archwires 3242d while maintaining a continuous action against the archwire.

One of the problems associated with this passive, straight clip design is that the archwire is loose within the archwire slot.

One modification of the Voudouris patent, to aide in the problem the passive clip resulting in looseness of the archwire in the slot mentioned above is addressed by United States Patent Publication No. 2011/007663 published Mar. 31, 2011 to Bryant et al. This application provides for a slidable shim member (referred to therein as clip 20 shown in FIG. 1) slidable into two outer tracks extending in an occlusal-gingival direction on the outer lateral surfaces of the bracket, with a vertical trough extending in an occlusal-gingival direction between the outer tracks. The shim has two parallel outer arms and a central tongue between the outer arms. The outer tracks of the bracket slidably engage the outer arms of the clip and the central tongue is slidably engaged by the vertical trough of the bracket, thereby allowing the clip to slidably move between an open position in which the outer arms of the clip are retracted and a closed position in which the outer arms of the clip extend across the archwire slot to retain the archwire in the archwire slot.

One problem associated with the Bryant et al. disclosure is that the shim prevents movement of the archwire out of the archwire slot, but, depending on the size of the archwire being used, the shim generally is not in contact with the archwire and thus there is still movement or looseness of the archwire within the archwire slot, as is illustrated in FIG. 5 of this disclosure. This results in a lower torque being applied to the archwire by the bracket overall as there is typically no contact between the shim and the archwire.

There is therefore a need in the art for a self-ligating orthodontic bracket having active archwire retention that addresses one or more of the aforementioned problems with the prior art.

SUMMARY OF THE INVENTION

The invention provides for a resilient locking shutter member slidable into two outer tracks angled gingivally and extending in an occlusal-gingival direction on the outer lateral surfaces of the bracket, with a preferably angled occlusal gingival opening forming a lingual vertical slot in relation to the labial surface of the bracket extending in an occlusal-gingival direction between the mesial and distal tie-wings and outer tracks, and that can be also angled in a gingival direction with respect to the vertical plane of the tooth. The resilient locking shutter member preferably has two parallel outer arms and a lingual guide bar in relation to the labial surface of the bracket between the outer arms. The outer tracks of the bracket slidably engage the outer arms of the clip and the lingual guide bar is slidably engaged by the occlusal gingival opening forming a lingual vertical slot of the bracket, thereby allowing the clip to slidably move between an open position in which the outer arms of the clip are retracted permitting positioning and removal of the archwire, and a closed position in which the outer arms of the clip extend across the archwire slot to retain the archwire in the archwire slot. The angling of the resilient locking shutter member within the angled outer tracks permits for contact between the resilient locking shutter member and an archwire in the archwire slot more often with round wires than passive systems for earlier rotation control and levelling. This contact occurs even more constantly with the progression to larger rectangular archwires to reach contact with the largest rectangular archwire at all times for greater torque control in the final, finishing stage. Furthermore, since the resilient locking shutter member is preferably made of a resilient nickel-titanium, chromium-cobalt, or spring steel material or alternatively any resilient material it can contact the archwire and home it toward the base of the slot by applying a lingual force along with a mild vertical vector. It should also be noted that resiliency is secondly, derived from shape design. The locking shutter has a U-shaped design that generates uniquely, further resiliency. Thereby, the locking shutter made of resilient material, and with its specialized, open U-shape for additional resiliency as herein disclosed is able to flex uniquely labial-lingually and/or mesio-distally.

With the above in mind, according to one embodiment of the invention, there is provided an orthodontic bracket having a body including a bonding base for attachment to the tooth, a lingual vertical slot, a pair of laterally spaced gingival tie wings and a pair of laterally spaced occlusal tie wings, the gingival and occlusal tie wings projecting from a labial surface of the body; an archwire slot extending mesio-distally across the body and between the gingival and occlusal tie wings at opposed medial and distal sides of the body to accommodate an archwire; a locking shutter including at pair of resilient arm members and a lingual guide bar between the resilient arm members, the locking shutter moveable between an open position in which placement and removal of the archwire is facilitated and a closed position in which placement and removal of the archwire is inhibited; first and second tracks formed on each of first and second outer lateral surfaces of the body, extending from the gingival tie wings across the archwire slot and into the occlusal tie wings; the first and second tracks sized and otherwise dimensioned to receive the pair of resilient arm members therein; wherein the first and second tracks extend in a substantially occlusal-gingival direction, angled gingivally by an angle θ with respect to a plane parallel with the vertical plane of a tooth on the outer lateral surfaces such that the first and second tracks.

According to an aspect of this embodiment, angle θ is between 5 and 75 degrees in a gingival direction with respect to a plane parallel with a surface of the tooth. The angle θ may also be between 30 and 75 degrees, and preferably between 35 and 65 degrees.

According to another aspect of this embodiment, the first and second tracks start from the occlusal aspect of the bracket and extend substantially parallel to one another, and diagonally across the archwire slot at a distance labial to the base of the archwire slot so that an archwire can be secured in the archwire slot as the pair of resilient arms slides in the tracks.

According to another aspect of this embodiment, the tracks start at a position closer to the labial surface portion of the occlusal tie wings and extend angularly in a gingival direction such that end portions of the tracks are located in a more lingual portion of the occlusal tie wings.

According to another aspect of this embodiment, the lingual guide bar further includes a depressed tongue portion extending towards the bonding base to snap-fit the resilient locking shutter into a locked position.

According to another aspect of this embodiment, the tracks further comprise depressions formed at gingival ends thereof; the locking shutter further comprises a protrusion formed on each of the arms; the depressions sized and otherwise dimensioned to receive the protrusions therein such that the protrusions compress into the depressions when the locking shutter is in the closed position.

According to another aspect of this embodiment, the resilient arms and the lingual guide bar are curved in convex to a base of the archwire slot, and the tracks are correspondingly curved to received the curved resilient arms there.

According to another aspect of this embodiment, the archwire has one of a round or a rectangular cross-section.

According to a second embodiment of the invention, there is provided an orthodontic bracket having a body including a bonding base for attachment to the tooth, a lingual vertical slot, a pair of laterally spaced gingival tie wings and a pair of laterally spaced occlusal tie wings, the gingival and occlusal tie wings projecting from a labial surface of the body; an archwire slot extending mesio-distally across the body and between the gingival and occlusal tie wings at opposed medial and distal sides of the body to accommodate an archwire; a locking shutter including at pair of resilient arm members and a lingual guide bar between the resilient arm members, the locking shutter moveable between an open position in which placement and removal of the archwire is facilitated and a closed position in which placement and removal of the archwire is inhibited; first and second tracks formed on each of first and second outer lateral surfaces of the body, extending from the occlusal tie wings across the archwire slot and into the gingival tie wings; the first and second tracks sized and otherwise dimensioned to receive the pair of resilient arm members therein; wherein the first and second tracks extend in a substantially occlusal-gingival direction, angled occlusally by an angle θ with respect to a plane parallel with the vertical plane of a tooth on the outer lateral surfaces such that the first and second tracks.

According to one aspect of this second embodiment, the first and second tracks start from the gingival aspect of the bracket and extend substantially parallel to one another, and diagonally across the archwire slot at a distance labial to the base of the archwire slot so that an archwire can be secured in the archwire slot as the pair of resilient arms slides in the tracks.

According to another aspect of this second embodiment, the tracks start at a position closer to the labial surface portion of the gingival tie wings and extend angularly in an occlusal direction such that end portions of the tracks are located in a more lingual portion of the gingival tie wings.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings.

DETAILED DESCRIPTION

Figure 1:
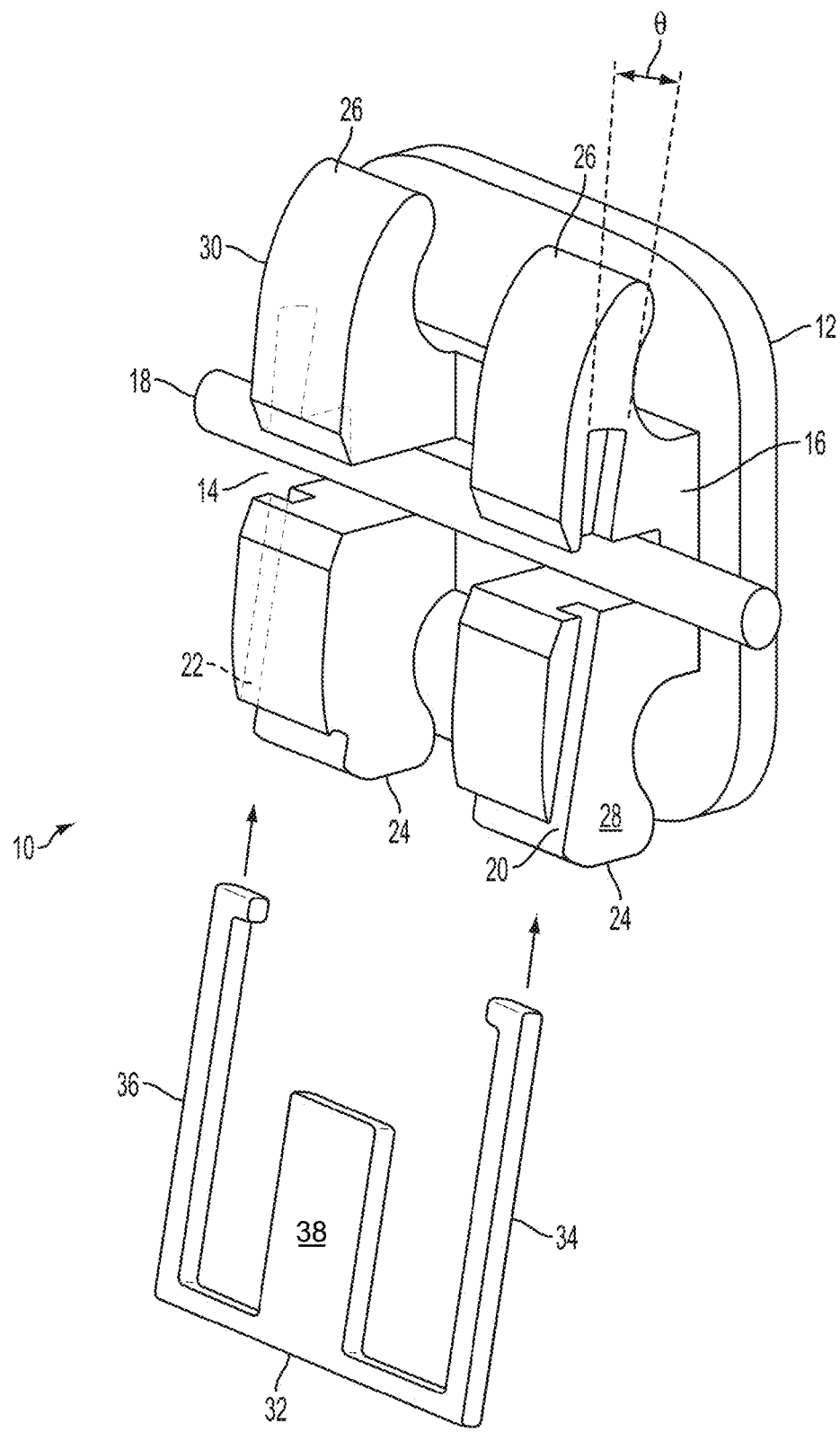
FIG. 1 is a perspective view of one embodiment of the invention, with the locking shutter in an open position.

Referring now to the FIG. 1, there is shown one embodiment of the self-ligating bracket according to the invention in which an orthodontic bracket 10 is provided having a bonding pad 12 for attachment to a tooth (not shown). An archwire slot 14 extends in a substantially medio-distal direction across the body 16 of the bracket 10 with an open labial aspect to receive an archwire 18. Occlusal tie wings 24 and gingival tie wings 26 are provided on opposed sides of the body 16. These elements are not described in more detail as their purpose and functioning is generally known in the art.

Figure 3:
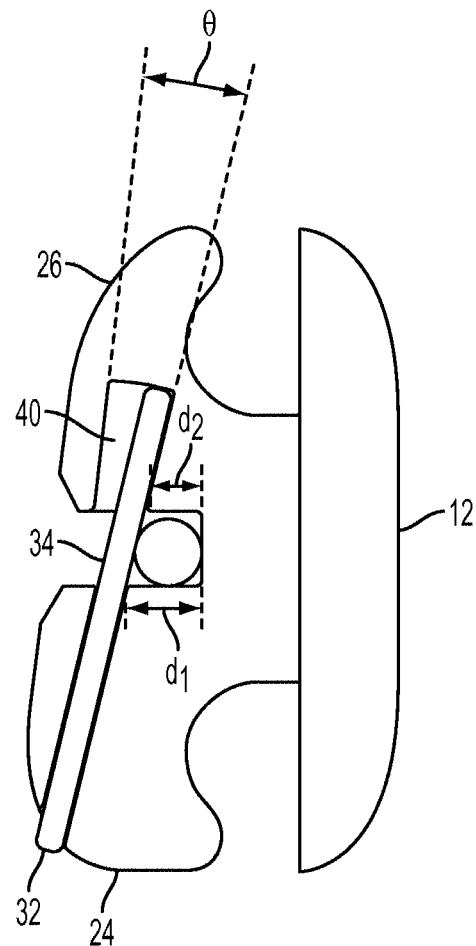
FIG. 3 is a side view of the embodiment of FIG. 2.

In this embodiment of the invention, two outer tracks 20 and 22 extend in a substantially occlusal-gingival direction, angled gingivally by angle θ (shown in FIG. 1, and more clearly in FIG. 3) with respect to a plane parallel with the vertical plane of a tooth on the outer lateral surfaces 28, 30 of the bracket 10. One outer track 20 runs along the mesial surface 28, and the other outer track 22 runs along the distal surface 30 of the bracket 10. Both outer tracks 20 and 22 start from the occlusal aspect of the bracket 10 and extend substantially parallel to one another, and diagonally across the archwire slot 14 at a distance labial to the base of the archwire so that an archwire can be secured in the archwire slot 14 as arms 34 and 36 of a locking shutter 32 slides in these outer tracks 20 and 22. Locking shutter 32 is preferably a resilient locking shutter, made of materials that are generally known in the art. The location of the outer tracks 20 and 22 preferably starts closer to the labial surface portion of the occlusal tie wings 24, and extends angularly in a gingival direction such that the end portions of the outer tracks 20 and 22 reside in a more lingual portion 40 of the gingival tie wings 26, as illustrated in FIG. 3. In this manner, the tracks 20 and 22 have little or no room for movement in the occlusal tie wings 24, and more room for movement in the gingival tie wings 26. This permits adaptation for different sized archwires 18 by permitting the ultimate angle of the locking shutter 32 to vary slightly.

Figure 2:
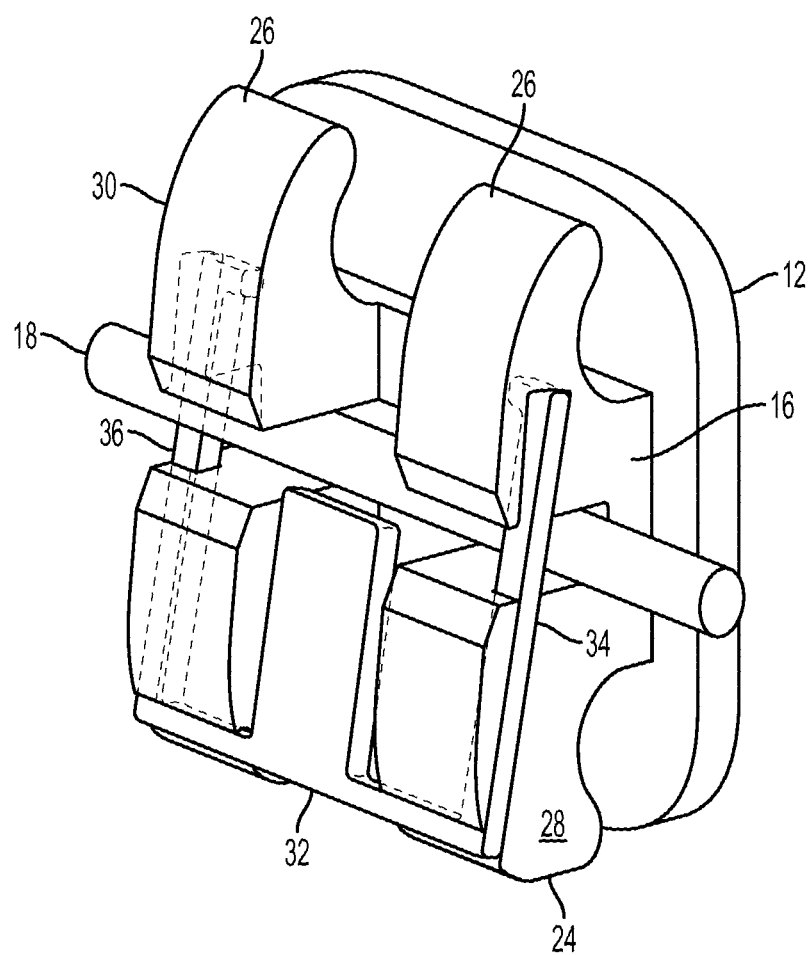
FIG. 2 is a perspective view of the embodiment of FIG. 1, with the locking shutter in the closed position.

This orientation of the outer tracks can also be reversed from those described above in the occlusal and gingival wings, where the resilient locking shutter 32 can open for instance upward toward the gingival tie wings. In addition, this can similarly occur in the lower brackets where the tracks start on the occlusal wings closer to lingual and angle toward the more labial surface in the gingival wings where the locking shutter opens downward toward the gingival wings. FIGS. 2 and 3 illustrate the locking shutter 32 of FIG. 1 in the in-use position, inserted into the tracks 20 and 22, and applying an active force onto the archwire 18 in a direction towards the base of the archwire slot 14.

The resilient locking shutter 32 is preferably formed from a resilient nickel-titanium, chromium-cobalt or spring steel material, or alternatively any resilient material that can apply a force to the archwire within the archwire slot as herein described.

Figure 4:
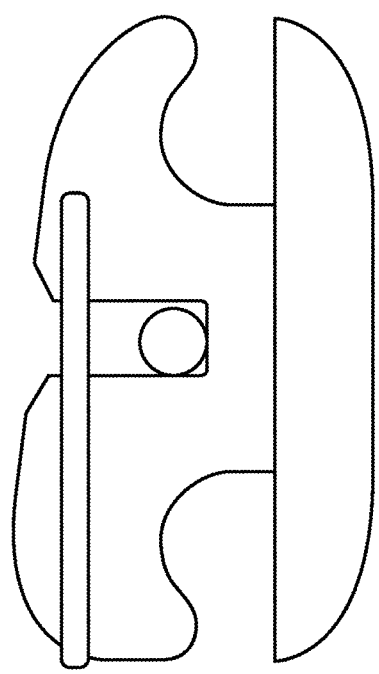
FIG. 4 is a side view of a prior art orthodontic bracket.

Preferably, the distance from the more labial portion of the occlusal tie wings 24 where the outer tracks 20 and 22 begin, the specific angle at which the outer tracks 20 and 22 extend, and the distance from the more lingual portion of the gingival tie wings 26 where the outer tracks 20 and 22 may be determined based on the particular size of archwire being used, the patient's oral physiology and other related factors. These distances and angles are determined such that an archwire in the archwire slot can be subjected to a force by the resilient locking shutter member In some preferred examples, the angle θ at which the outer tracks 20 and 22 extends is between 5 and 75 degrees in a gingival direction with respect to a plane parallel with a surface of the tooth, preferably, the angle is between 30 and 75 degrees, and more preferably between 35 and 65 degrees. In particular, the distance from the floor or base of the archwire slot 14 to a position where the outer tracks 20 and 22 cross the archwire slot 14 will be approximately the same as, or marginally less than the width or depth of a rectangular archwire 18. This distance is shown as d1 and d2 on alternate sides of the archwire slot 14 in FIG. 3. As will be appreciated by one skilled in the art, irrespective of the size, and in particular the cross-sectional width, of the archwire 18, the angled tracks of the invention enable the locking shutter to actively apply a force onto the archwire 18, and therefore to maintain a prerequisite tension on the archwire 18 within the slot 14. In contrast, FIG. 4 shows a cross section of a prior art bracket and locking shutter, where the locking shutter extends in parallel with the bonding base. As can be seen, the archwire is able to move around in the slot of FIG. 4, and no adaptability or compensation can be provided for archwires of different sizes.

The resilient locking shutter 30 is sized and otherwise dimensioned to slidably engage the outer tracks 20 and 22, and to extend angularly therethrough as illustrated. The resilient locking shutter 30 preferably includes outer arms 32 and 34 designed and adapted to correspond dimensionally with the outer tracks 20 and 22 such that the outer arms 32 and 34 may be slidably received in the outer tracks 20 and 22. Located at the gingival ends of the tracks 20 and 22 are small depressions 42. Depressions 42 are used for locking the two flexible and small, dome-like, protrusions 44 of the outer arms 32 and 34 when the resilient locking shutter closes. The outer arm protrusions 44 compress into the track depressions 42. The outer arms 32 and 34 also extend from a horizontal portion 36 of the resilient locking shutter member 30. Also preferably extending from the horizontal portion 36 is lingual guide bar 38 that extends between the outer arms 32 and 34. The lingual guide bar 38 is sized and otherwise dimensioned to slide into contact with the occlusal gingival opening or lingual vertical slot of the bracket 10 when the resilient locking shutter 30 is moved between the open (FIG. 1) and closed (FIG. 2) positions. The occlusal gingival opening or lingual vertical slot serves as a guide to maintain proper alignment of the locking shutter 30 with respect to the bracket 10 during assembly and movement of the resilient locking shutter 30. The lingual guide bar 38 helps to prevent the resilient locking shutter 30 from becoming wedged out of proper alignment with the outer tracks 20 and 22 which could otherwise result in damage to the resilient locking shutter 30. The occlusal gingival opening or lingual vertical slot is preferably wider and provides a degree of structural stability for the resilient locking shutter 30.

Figure 5A:
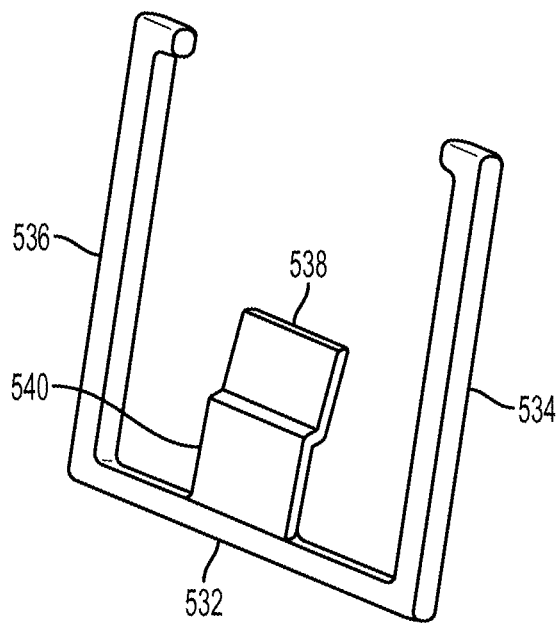
FIG. 5A is a perspective view of a locking shutter according to a second embodiment of the invention.
Figure 5B:
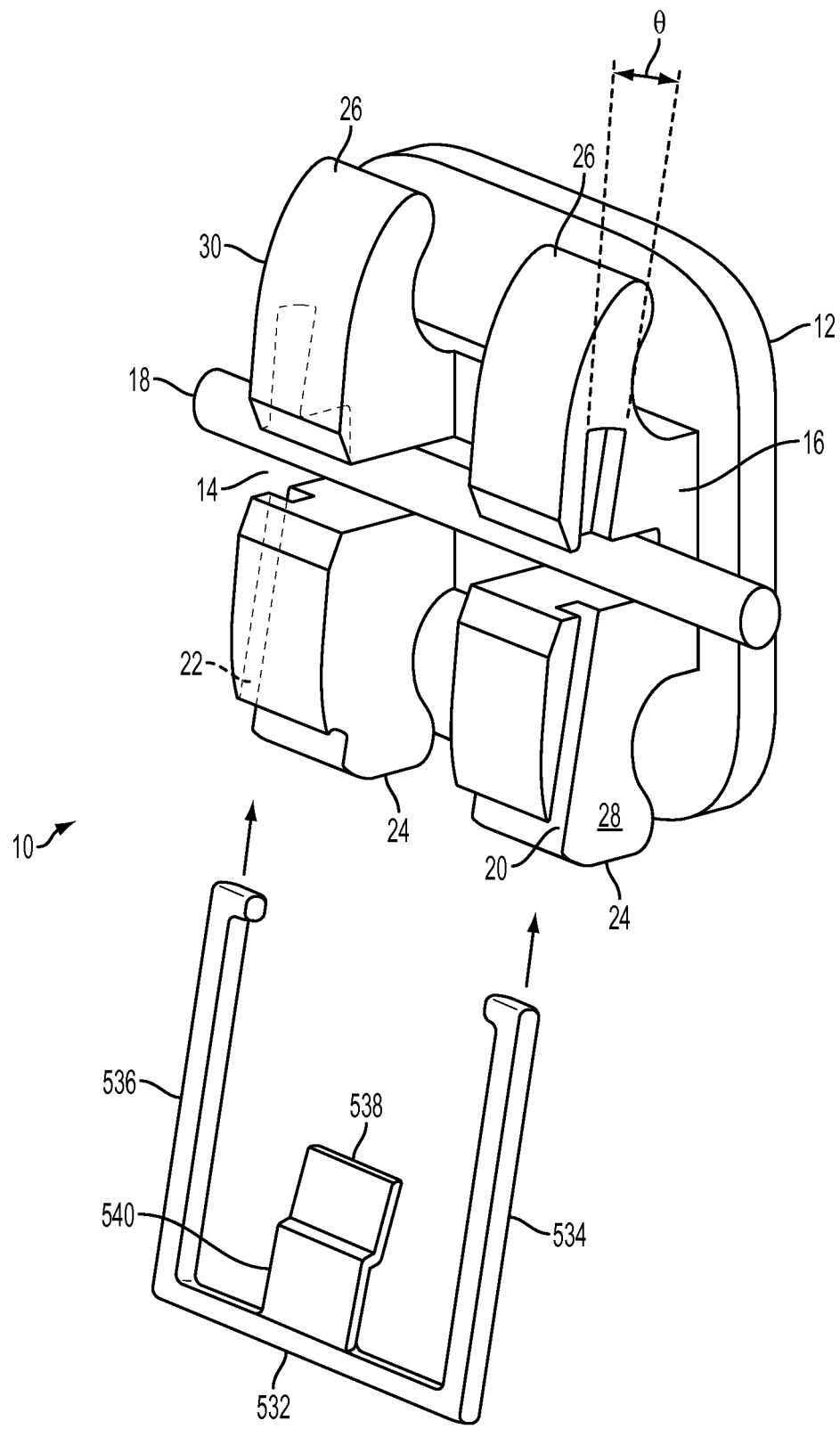
FIG. 5B is a perspective view of the second embodiment of the invention, with the locking shutter in an open position.
Figure 5C:
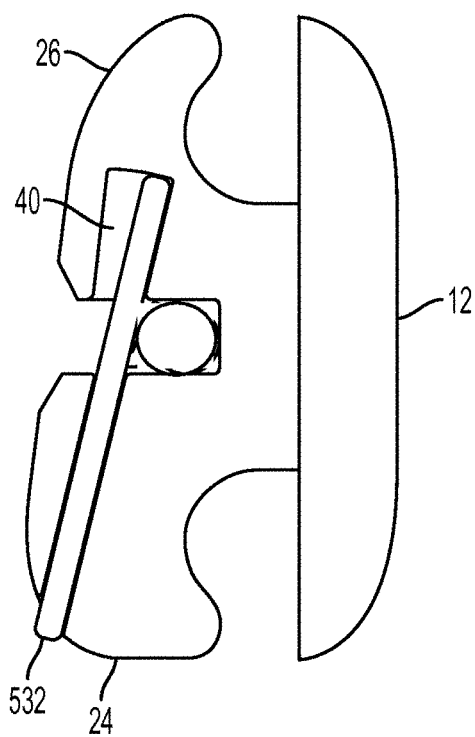
FIG. 5C is a side view of the embodiment of FIG. 5B, with the locking shutter in the closed position.

Referring now to FIGS. 5A-5C, there is shown another embodiment of the invention in which a locking shutter 532 is provided having arm portions 534 and 536, respectively. In FIG. 5, elements common with those of the embodiment of FIGS. 1-3 are correspondingly numbered, and reference is made to the description above for an identification of these elements. Those elements that differ are now discussed. Locking shutter 532 includes, in addition to arm portions 534 and 536, a depressed tongue portion 538 extending towards the bonding base 12 from the lingual guide bar 540 to snap-fit the resilient locking shutter 530 into a locked position.

When combined with the angled tracks 20 and 22, the locking shutter 532 having the depressed portion permits more flexibility in the range of sizes of the archwire that may be used, while still maintaining the active application of force made possible by the invention herein described.

Figure 6:
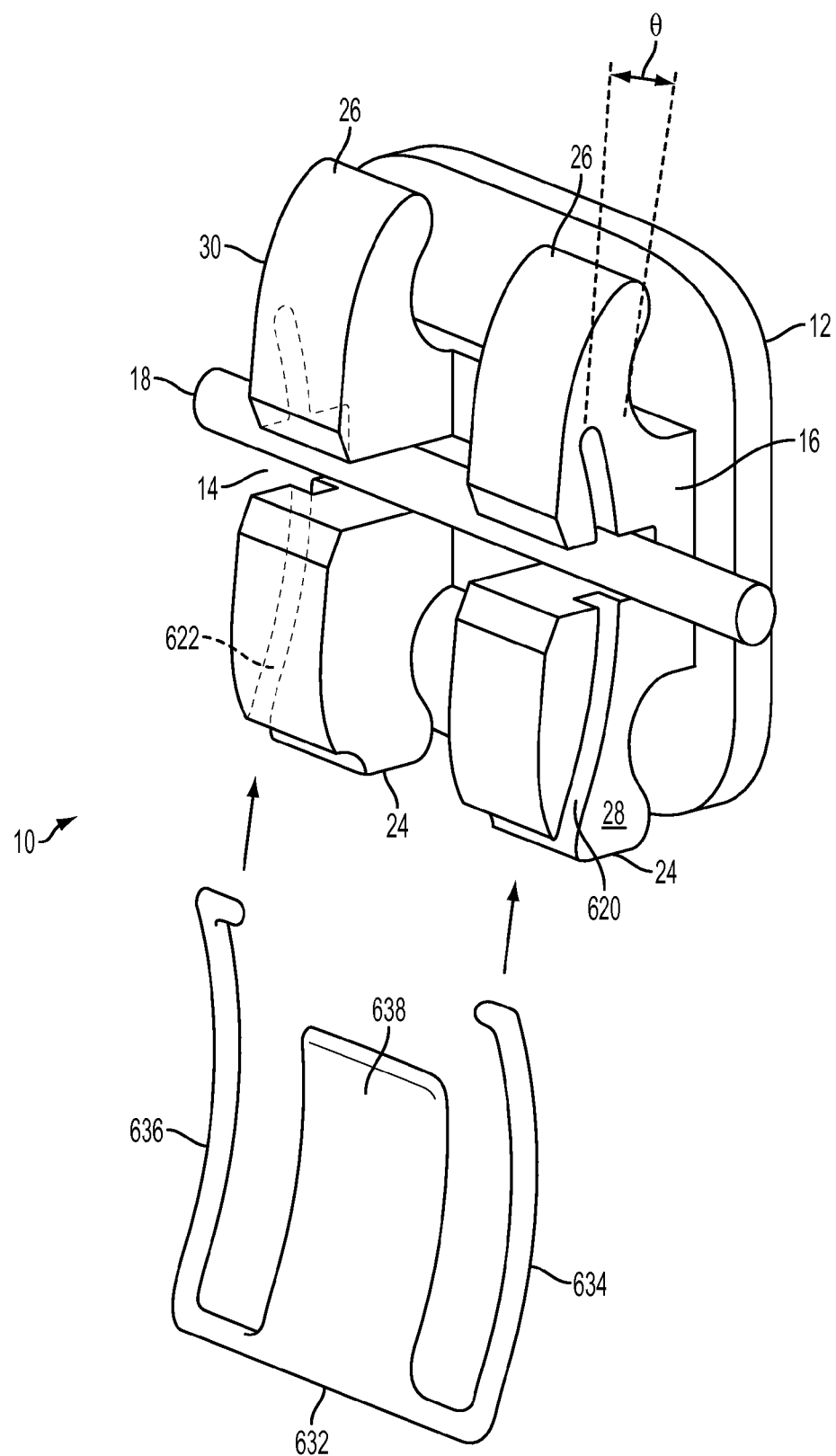
FIG. 6 is a perspective view of a third embodiment of the invention, with the locking shutter in an open position.
Figure 7:
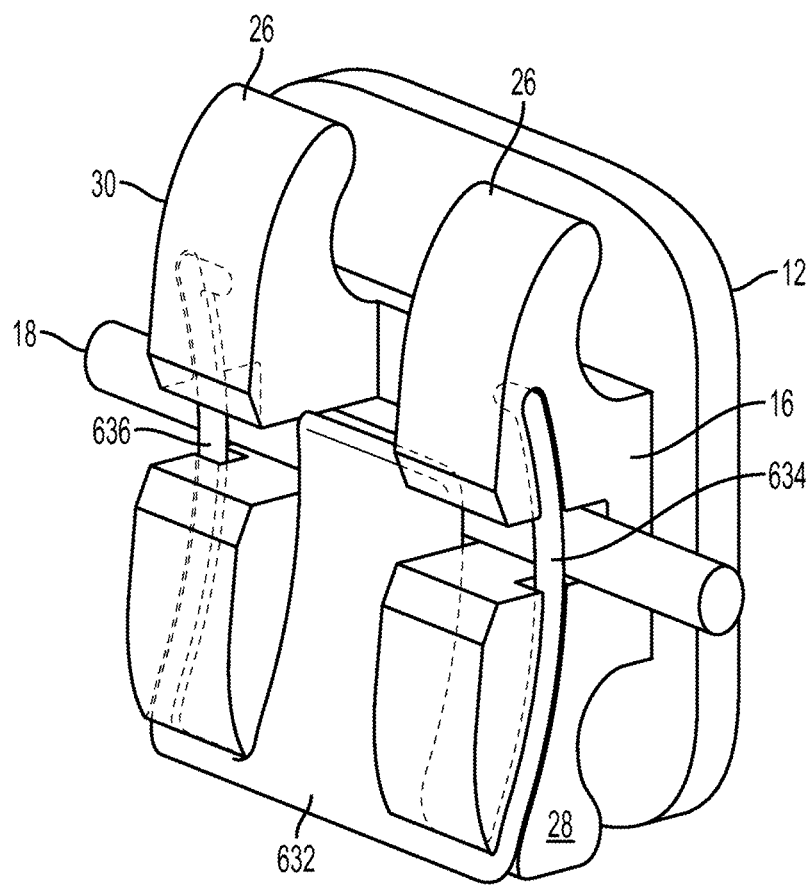
FIG. 7 is a perspective view of the embodiment of FIG. 6, with the locking shutter in the closed position.
Figure 8:
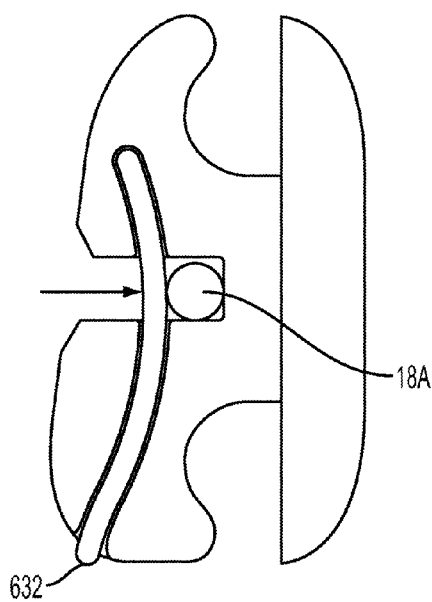
FIGS. 8 and 9 are side view of the embodiment of FIG. 7, with round and square archwires, respectively.
Figure 9:
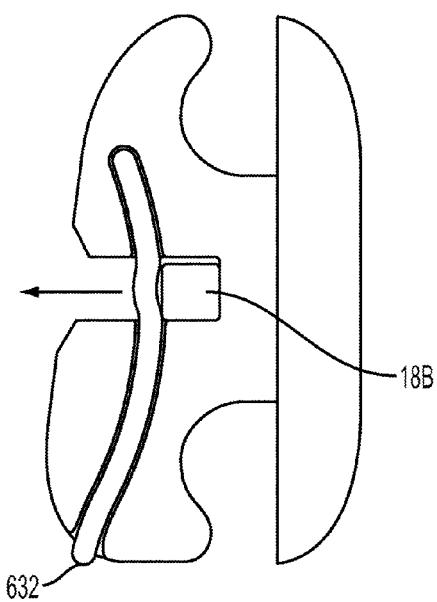

Referring now to FIGS. 6 and 7, there is shown yet another embodiment of the invention, in which the locking shutter 632, including the arms 634, 636 and the lingual guide bar 638 are mildly curved in convex to the base of the slot 14. To accommodate this, angled tracks 620 and 622 are correspondingly curved, in addition to being angled slightly as per the embodiment of FIG. 1. One of the advantages of the curved tracks 620, 622 of the bracket body, and curved arms 634, 636 of the resilient locking shutter is the ability to accommodate archwires of different cross-sectional shapes and sizes. In particular, during orthodontic treatment, it is common that during the early stages of treatment, an archwire of circular cross-section 18A, shown in FIG. 8, is used. During later stages of treatment, an archwire of square or rectangular cross-section 18B is used, as shown in FIG. 9. The curved locking shutter 632 enables contact of both round wires initially and larger rectangular wires during the finishing stages of orthodontic treatment, as illustrated in FIGS. 8 and 9. Furthermore, this embodiment permits tracks 620 and 622 to be sized correspondingly with the locking shutter 630 in both the occlusal and gingival tie wings. The ability to accommodate different sized archwires arises from the curvature in the locking shutter. With rectangular wires the curved outer arms will level mildly while still maintaining the angle position, as illustrated in FIG. 9. It is noted that the drawing in FIG. 9 is shown with deformations exaggerated for ease of understanding.

As will now be apparent to a person skilled in the art, the angled positioning of the resilient locking shutters as herein described within the angled outer tracks results in an active self-ligating bracket that permits early and more constant contact between the resilient locking shutter (and therefore the bracket) and the archwire itself. Second, both the bracket tracks and the corresponding outer arms can additionally be curved toward the base of the slot so as to produce light, and continuous contact with both round wires initially and rectangular wires during finishing. Third, It should also be noted that the resilient locking shutter has a unique generally U-shape that makes it a more flexible design. This design or shaping for resiliency is additive to the actual resilient material used for overall greater flexibility. The locking shutter as herein disclosed is able to be highly flexible labial-lingually and/or mesio-distally. This can be observed by flexing the locking shutter easily between the fingers.

Furthermore, the design fourthly, shows a resilient locking shutter that is unique. In contrast to prior art brackets, the present invention shows a locking shutter positioned largely outside or bilateral to the bracket body with an open U-shape design making it more resilient. These factors produce the advantages of greater overall control of orthodontic tooth movement. The design also includes tracks on the outside of the bracket resulting in more flex permissible for the resilient locking shutter. Fifth, the design with a lateral, or outside-of-bracket position of the locking shutter as herein disclosed permits for a low profile bracket having a reduced thickness labial-lingually for patient comfort against the lips. This is enabled, at least in part, due to the active forces applied to the archwire by the angled locking shutter/track combination which reduces the size of the bracket required to provide the requisite forces on the archwire. This active force system as herein disclosed produces light, continuous forces on the dentition for more physiological and biological tooth movement for potentially fewer iatrogenic complications potentially such as root resorption. The various problems identified in the prior art may thereby be obviated with use of the invention by distinctly improving rotation control, sliding control and torque control for finishing with a more active self-ligating bracket.

Finally, it will be understood by one skilled in the art that the above described embodiments are presented as examples only, with various modifications and alternatives permitted within the spirit and scope of the invention, which is not to be considered limited by the specific embodiments disclosed.

The invention claimed is:

1. An orthodontic bracket comprising
   a body including a bonding base for attachment to the tooth, a pair of laterally spaced gingival tie wings and a pair of laterally spaced occlusal tie wings, said gingival and occlusal tie wings projecting from a labial surface of said body; an archwire slot extending mesio-distally across said body and between the gingival and occlusal tie wings at opposed medial and distal sides of said body to accommodate an archwire;
   a locking shutter including a pair of resilient arm members, said locking shutter moveable between an open position in which placement and removal of said archwire is facilitated and a closed position in which placement and removal of said archwire is inhibited;
   first and second tracks formed on each of first and second outer lateral surfaces of said body, extending from said gingival tie wings across said archwire slot and into said occlusal tie wings; said first and second tracks sized and otherwise dimensioned to receive said pair of resilient arm members therein;
   wherein said first and second tracks extend in a substantially occlusal-gingival direction, angled such that a distance from a base of the archwire slot to a position where the outer tracks cross the archwire slot is defined by distances d1 and d2 on alternate sides of the archwire slot; wherein d1 and d2 are different
   and wherein said first and second tracks have a labial-lingual thickness in said occlusal tie wings less than a labial-lingual thickness in said gingival tie wings.

2. An orthodontic bracket according to claim 1, wherein d1 and d2 define an angle θ between 5 and 75 degrees in a gingival direction with respect to a plane parallel with a surface of the tooth.

3. An orthodontic bracket according to claim 2, wherein angle θ is between 30 and 75 degrees, and preferably between 35 and 65 degrees.

4. An orthodontic bracket according to claim 1, wherein said first and second tracks start from the occlusal aspect of said bracket and extend substantially parallel to one another, and diagonally across said archwire slot at a distance labial to the base of said archwire slot so that an archwire can be secured in said archwire slot as said pair of resilient arms slides in said tracks.

5. An orthodontic bracket according to claim 4, wherein said archwire has one of a round or a rectangular cross-section.

6. An orthodontic bracket comprising a body including a bonding base for attachment to the tooth, a pair of laterally spaced gingival tie wings and a pair of laterally spaced occlusal tie wings, said gingival and occlusal tie wings projecting from a labial surface of said body; an archwire slot extending mesio-distally across said body and between the gingival and occlusal tie wings at opposed medial and distal sides of said body to accommodate an archwire;

a locking shutter including a pair of resilient arm members, said locking shutter moveable between an open position in which placement and removal of said archwire is facilitated and a closed position in which placement and removal of said archwire is inhibited;

first and second tracks formed on each of first and second outer lateral surfaces of said body, extending from said occlusal tie wings across said archwire slot and into said gingival tie wings; said first and second tracks sized and otherwise dimensioned to receive said pair of resilient arm members therein;

wherein said first and second tracks extend in a substantially occlusal-gingival direction, angled such that a distance from a base of the archwire slot to a position where the outer tracks cross the archwire slot is defined by distances d1 and d2 on alternate sides of the archwire slot; wherein d1 and d2 are different and wherein said first and second tracks have a labial-lingual thickness in said occlusal tie wings less than a labial-lingual thickness in said gingival tie wings.

7. An orthodontic bracket according to claim 6, wherein angle θ between 5 and 75 degrees in an occlusal direction with respect to a plane parallel with a surface of the tooth.

8. An orthodontic bracket according to claim 7, wherein angle θ is between 30 and 75 degrees, and preferably between 35 and 65 degrees.

9. An orthodontic bracket according to claim 6, wherein said first and second tracks start from the gingival aspect of said bracket and extend substantially parallel to one another, and diagonally across said archwire slot at a distance labial to the base of said archwire slot so that an archwire can be secured in said archwire slot as said pair of resilient arms slides in said tracks.

* * * * *